United States Patent [19]

Rand et al.

[11] Patent Number: 4,817,822

[45] Date of Patent: Apr. 4, 1989

[54] INDICATING DEVICE

[75] Inventors: Paul K. Rand, Hitchin; Carole A. Osterweil, Swiss Cottage; Robert E. Newell, Pinner, Middlesex, all of England

[73] Assignee: Glaxo Group Limited, London, England

[21] Appl. No.: 42,431

[22] Filed: Apr. 24, 1987

[30] Foreign Application Priority Data

Apr. 25, 1986 [GB] United Kingdom ............. 8610121
Aug. 11, 1986 [GB] United Kingdom ............. 8619516

[51] Int. Cl.$^4$ .............................................. B67D 5/22
[52] U.S. Cl. ............................. 222/38; 222/162; 222/185; 128/200.23
[58] Field of Search ............ 222/38, 36, 23, 31, 222/162, 185; 128/200.23; 221/2, 6–8; 116/266, 264, 307; 74/422, 424.6

[56] References Cited

U.S. PATENT DOCUMENTS

| | | | |
|---|---|---|---|
| 1,219,858 | 3/1917 | Patterson | 222/36 X |
| 2,455,962 | 12/1948 | Wheeler et al. | 222/38 |
| 2,630,027 | 3/1953 | Wunderlich | 74/424.6 |
| 3,119,557 | 1/1964 | Chapman | 222/36 X |
| 3,495,567 | 2/1970 | Hayes et al. | |
| 3,572,282 | 3/1971 | Tump et al. | |
| 3,655,952 | 4/1972 | Johnson et al. | 222/38 X |
| 4,188,984 | 2/1980 | Lyall | 222/38 |
| 4,350,265 | 9/1982 | Grittiths et al. | 222/38 |
| 4,565,302 | 1/1986 | Pfeiffer et al. | 222/38 |

FOREIGN PATENT DOCUMENTS

| | | | |
|---|---|---|---|
| WO86/02275 | 4/1986 | PCT Int'l Appl. | |
| 998148 | 7/1965 | United Kingdom | |
| 1290484 | 9/1972 | United Kingdom | |
| 1317315 | 5/1973 | United Kingdom | 222/38 |
| 2063075 | 6/1981 | United Kingdom | |
| 2092991 | 8/1982 | United Kingdom | |
| 2104393 | 3/1983 | United Kingdom | |

Primary Examiner—Joseph J. Rolla
Assistant Examiner—Gregory L. Huson
Attorney, Agent, or Firm—McAulay, Fields, Fisher, Goldstein & Nissen

[57] ABSTRACT

A device is described for indicating the number of doses dispensed from an aerosol container (2, 102) having an outlet valve member (4, 104) movable relative to the body of the container to dispense its contents in measured doses. Relative movement between the aerosol container body and the outlet member are detected by a ratchet wheel (14, 114) and ratchet driving member (11A, 111) which move with the body and outlet member respectively or vice versa. The ratchet wheel may in turn drive an indicating member in the form of a linear rack (20, 119, 120) or rotatable wheel (116).

11 Claims, 5 Drawing Sheets

INDICATING DEVICE

FIELD AND BACKGROUND OF THE INVENTION

The present invention relates to a device for indicating the number of doses dispensed from an aerosol container, and, also, to aerosol devices, for example, inhalation devices by which medicaments contained in an aerosol may be administered to a patient.

It is well known to treat patients with medicaments contained in an aerosol, for example, in bronchodilator therapy. It is also known to use for such therapy, medicaments which are contained in an aerosol and are administered to a patient by means of an inhalation device comprising a tubular housing or sleeve in which the aerosol container os located and an outlet tube leading out of the tubular housing. The aerosol containers used in such inhalation devices have an outlet valve member at one end which can be opened either by depressing the valve member while the container is held stationary or by depressing the container while the valve member is held stationary. In the use of such devices, the aerosol container is placed in the tubular housing with the outlet valve member of the container communicating via a support with the outlet tube, for example, a nozzle or mouthpiece. When used for dispensing medicaments, for example in bronchodilation therapy, the housing is then held by the patient in a more or less upright condition and the mouthpiece or nozzle of the inhalation device is placed in the mouth or nose of the patient. The aerosol container is pressed towards the support to dispense a dose of medicament from the container which is then inhaled by the patient.

A disadvantage arising from use of such known devices is that the patient cannot determine the amount of medicament in the aerosol container at any given time. In an extreme case this could mean that the patient, possibly suffering from severe bronchospasm and needing a dose of medicament, will find that the aerosol container will not dispense a dose because its contents have already been exhausted.

BRIEF SUMMARY OF THE INVENTION

An object of the present invention is to provide means of overcoming this disadvantage.

Accordingly, the present invention provides a device for indicating the number of doses dispensed from an aerosol container having a body and an outlet member movable relative to the body to dispense its contents in measured doses, said device comprising movement detection means responsive to relative movement between the body and the outlet member, and indicating means responsive to the movement detection means so that the indicator means is indicative of the number of movements of the body relative to the outlet member and, therefore, of the quantity of the contents of the container remaining therein or which have been discharged therefrom.

The device of the present invention is preferably adapted for removable mounting to an aerosol container located in the housing of the medical inhalation device.

In one preferred embodiment, an actuator member is provided which comprises a ring-form member for mounting to the body of the aerosol container. A further member is provided which during at least a portion of the movement of the actuator member, is held stationary with respect to the outlet member. In a preferred embodiment, this further member is held stationary by abutment with a housing in which the aerosol container is received and in which the outlet member of the aerosol container is supported during relative movement of the container body.

The device preferably comprises a ratchet wheel which is caused to rotate, by relative movement between the container body and the container housing, through a pre-determined angle. This wheel may itself bear markings to indicate the number of relative movements made between the aerosol container and outlet member but is preferably adapted to drivde, for example, an indicator rack or toothed wheel bearing such markings, employing a suitable step-down gear ratio. This latter arrangement permits the number of doses indicated to exceed many times the number of teeth on the ratchet wheel and, hence the production of a compact device.

According to a further aspect of the present invention there is provided an aerosol dispensing device comprising a housing in which an aerosol container can be located, an outlet leading from the housing and a support in the housing arranged to receive an outlet member of the aerosol container and having a passage through which the contents of the aerosol container may pass to the outlet, the aerosol dispensing device being provided with a dose indicating device according to the invention.

BRIEF DESCRIPTION OF THE INVENTION

Embodiments of the present invention will now be described with reference to the accompanying drawings in which:

FIG. 2b shows a view, from the opposite side to FIG. 2 of a feature applicable both to the embodiment of FIGS. 1 and 2, and the modified embodiment of FIG. 2a;

Figure 3:
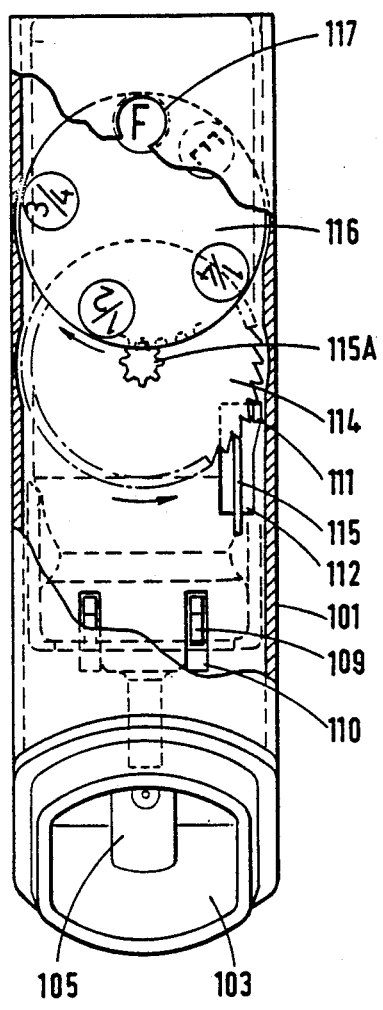
FIG. 3 is a front view of a further embodiment of the invention, part of a front wall of the device being broken away.
Figure 4:
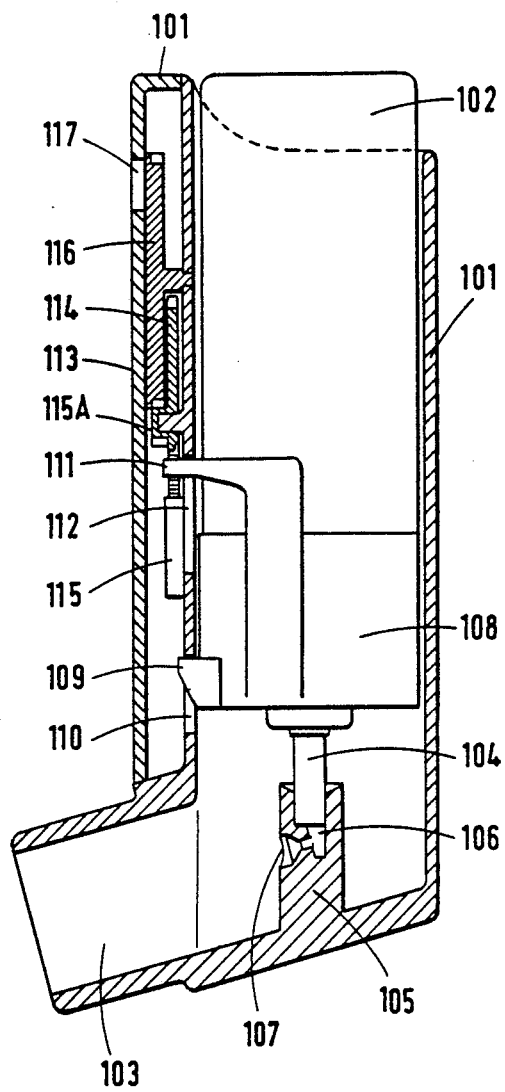
FIG. 4 is a sectional view of the device of FIG. 3.
Figure 5:
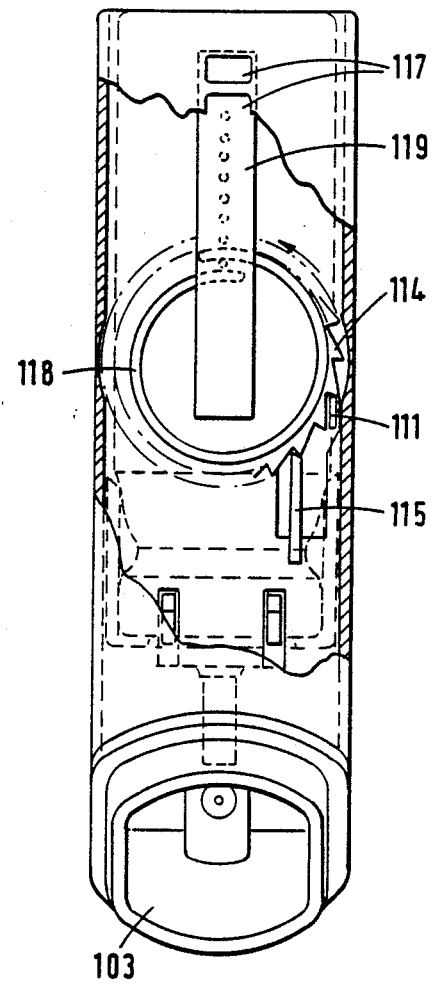
Figure 6:
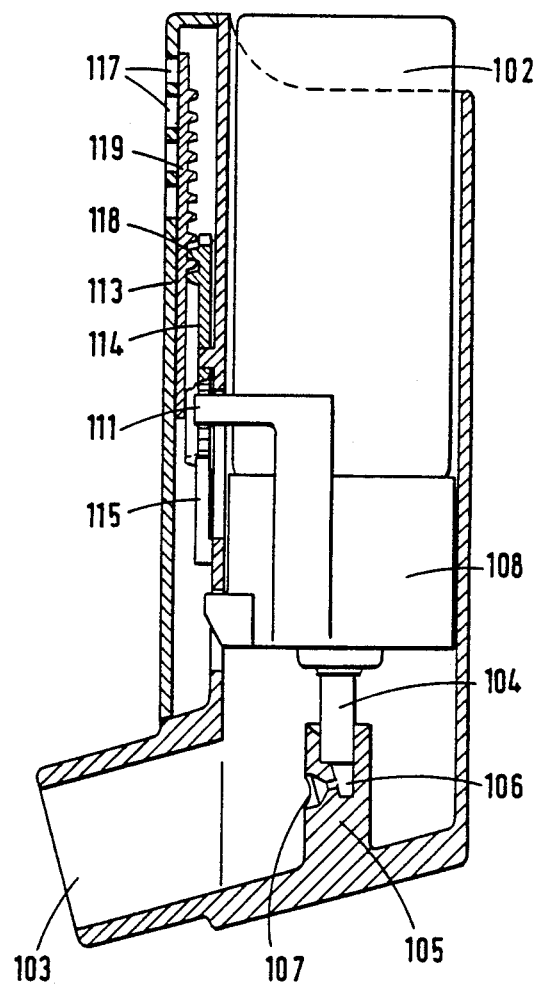
Figure 7:
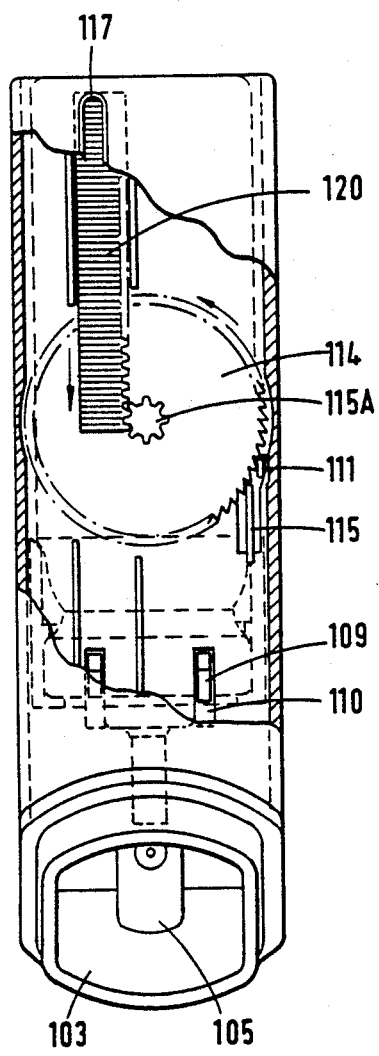
Figure 8:
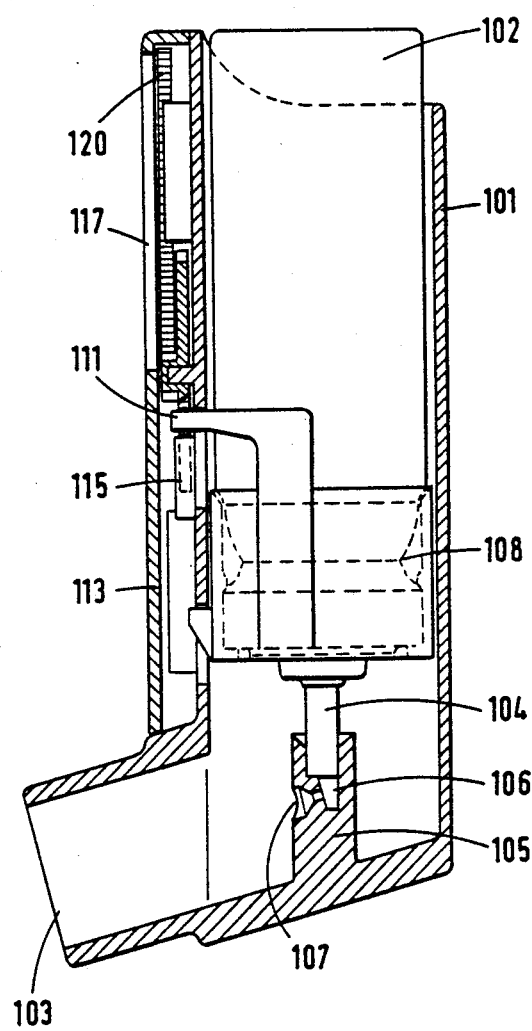

FIGS. 5 and 6 are similar views illustrating one modification of the device illustrated in FIGS. 3 and 4; and FIGS. 7 and 8 are similar views of another modification.

DETAILED DESCRIPTION OF PREFERRED EMBODIMENTS

Figure 1:
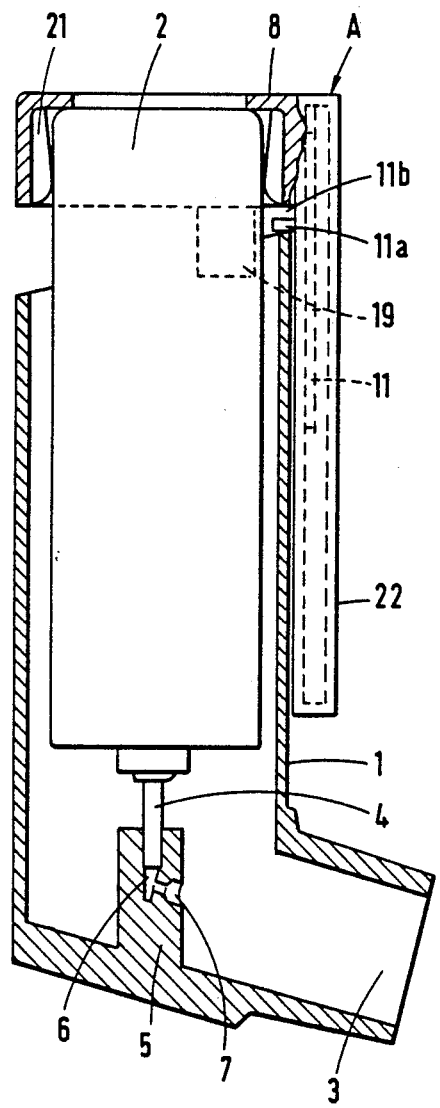
FIG. 1 is a side view, partially in section, of a first embodiment of the indicating device of the present invention mounted to a medical inhalation device.
Figure 2:
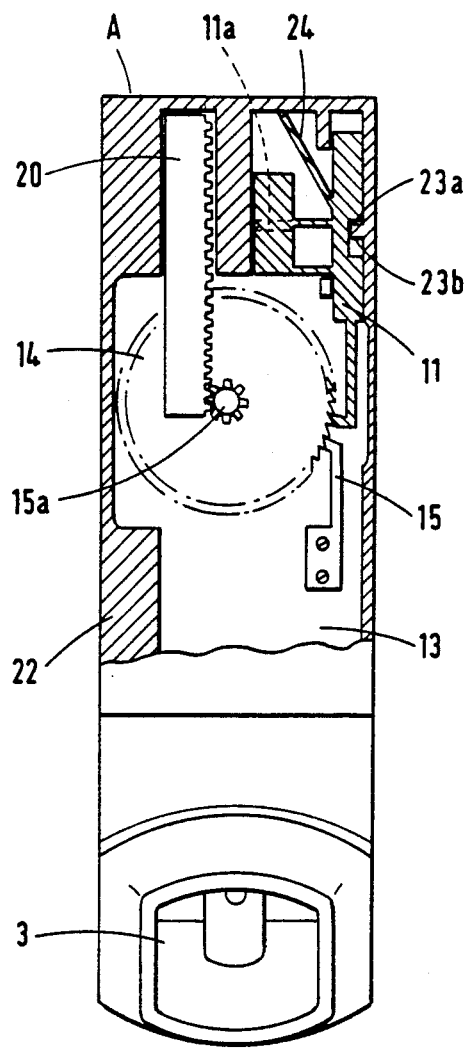
FIG. 2 is a front view of the arrangement shown in FIG. 1 in which the indicating device is shown in section.

The inhalation device shown in FIGS. 1 and 2 comprises a tubular housing 1 in which an aerosol container 2 can be located. The housing is open at one end (which will hereinafter be considered to be the top of the device for convenience of description) and is closed at the other. An outlet 3 leads laterally from the closed end of the housing 1. In the embodiment illustrated, the outlet 3 is in the form of a mouthpiece intended for insertion into the mouth of the patient, but it may, if desired, be designed as a nozzle for insertion into the patient's nostril.

The aerosol container 2 has an outlet valve member 4 at one end. This valve member can be depressed to release a measured dose from the aerosol container or, alternatively, the valve member 4 can be fixed and the main body of the container can be moved relative to the valve member to release the dose.

As shown clearly in FIG. 1, the aerosol container 2 is located in the housing 1 so that one end protrudes from its open top. Spacer ribs (not shown) may be provided inside the housing to hold the external surface of the contaienr 2 spaced from the internal surface of the housing 1. A support 5 is provided at the lower end of the housing 1 and has a passage 6 in which the valve member 4 of the aerosol container 2 can be located and supported. A second passage 7 is provided in the support 5 and is directed towards the interior of the outlet 3. Thus, when the parts are in the positions shown in FIGS. 1 and 2, the protruding portion of the aerosol container 2 can be depressed to move the container relative to the valve member 4 to open the valve and a dose of medicament contained in the aerosol will be discharged through the passage 7 and into the outlet 3 from which it can be inhaled by a patient. One dose will be released from the aerosol container each time it is fully depressed.

FIGS. 1 and 2 also show an embodiment of the dose indicating device of the present invention. This device A comprises an actuator member in the form of a ring-shaped cap member 8 which is removably located on the end of the protruding portion of the body of the aerosol container 2. The cap member 8 is retained on the body of the aerosol container 2 by means of longitudinal ribs 21 on its internal surface so that once it is on the body it cannot be removed too easily. The top of the cap abuts the end of the body of the container 2 and moves with the body throughout its displacement towards and away from the support 5. A pair of symmetrically placed spacing elements 19, of which one can be seen in FIG. 1, extend from the lip of the cap member 8 into the housing 1 and slide against the internal wall of this housing so as to guide the movement of the aerosol container body therein.

Attached to the side of the cap member 8 and movable therewith is a housing 22 which defines an indicator compartment 13. This housing 22 extends from the cap member 8 along the external surface of the tubular housing 1. The length of this indicator housing 22 is such that when mounted to the tubular housing 1, it does not abut the outlet 3 as it moves downwardly with the container body.

A driving arm 11 is slidably retained within the housing 22 and is guided for movement between two limit positions defined by stop surfaces 23a and 23b. The driving arm 11 supports a projection 11a which extends through and is movable within a slot 11b in the wall of the indicator housing 22 mounted adjacent the tubular housing 1. In this embodiment, projection 11a rests on the top edge 1a of the wall of the tubular housing 1.

The driving arm 11 engages a ratchet wheel 14 which is mounted to the wall of the indicator housing 22. This ratchet wheel cooperates with a ratchet pawl 15. Whenever the body of the aerosol container 2 is depressed to open the valve member 4, the ratchet wheel 14 moves downwards with the cap member 8 while the driving arm 11 remains stationary with respect to the support 5 by virtue of the abutment of projection 11a with the wall of the tubular housing 1. In view of the engagement of the driving arm 11 with the ratchet wheel 14, this relative linear movement between these two elements results in rotation of the ratchet wheel 14 in an anticlockwise direction (as viewed in FIG. 2) through the angle subtended by a ratchet wheel tooth.

A spur wheel 15a which is rotatable with the ratchet wheel 14, engages a toothed indicator rack 20. The gear ratio between the ratchet and spur wheel is such that the indicator rack moves through one "step" for a predetermined number of ratchet wheel "steps" and, hence, doses dispensed.

The front of the housing 22 has a window (not shown) through which a portion of the indicator rack 20 is visible. This indicator rack carries suitable markings which are displayed through the window when the given marking registers with this window. Any suitable markings may be employed, though preferably not letters, numbers or like characters which require to be read. For example, the rack can be marked with different colours of different portions so that, for example, when a red portion is displayed through the window, the patient will know that a new aerosol container must be obtained. In other alternatives, however, the indicator rack may be marked with numbers to indicate the proportion of the contents still remaining or the number of doses dispensed from or remaining in the aerosol container. In a convenient arrangement, the markings on the indicator rack indicate that the aerosol container is empty after a predetermined number of doses, for example 200, have been dispensed, this predetermined number being less than the number of doses with which the container has been charged, say 220, so as to allow for a margin of error.

With displacement of the cap member 8 and housing 22 towards the support 5, a resilient member 24 attached to or part of driving arm 11, extends obliquely between the driving arm 11 and the top wall of the housing 22 is placed under compression and distorts. Once the pressure applied to the member 8 has been released, the device A returns to the position illustrated in FIGS. 1 and 2. The force exerted by the resilient member 24 pushes the driving arm 11 downwards within the housing 22 so as to engage a subsequent tooth of the ratchet wheel 14.

The device illustrated in FIGS. 1 and 2 may be modified by replacing the indicator rack 20 by a toothed indicator wheel which is engaged by the spur wheel 15A. Thus, on rotation of the ratchet wheel 14 the spur wheel 15A drives this indicator wheel.

In a further modification of the device illustrated in FIGS. 1 and 2, the spur wheel 15A is replaced on the ratchet wheel 14 by a single start worm and the toothed indicator rack 20 is replaced by an indicator rack having a row of projections engageable by this single start worm. Thus, in this case, rotation of the ratchet wheel 14 rotates the single start worm which in turn drives the indicator rack.

Figure 2A:
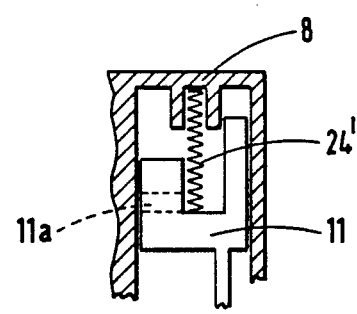
FIG. 2a shows part of modified embodiment from one side.

FIG. 2a shows a modification of part of what is shown in FIG. 2, the resilient member 24 being replaced by a compression spring 24'.

Figure 2B:
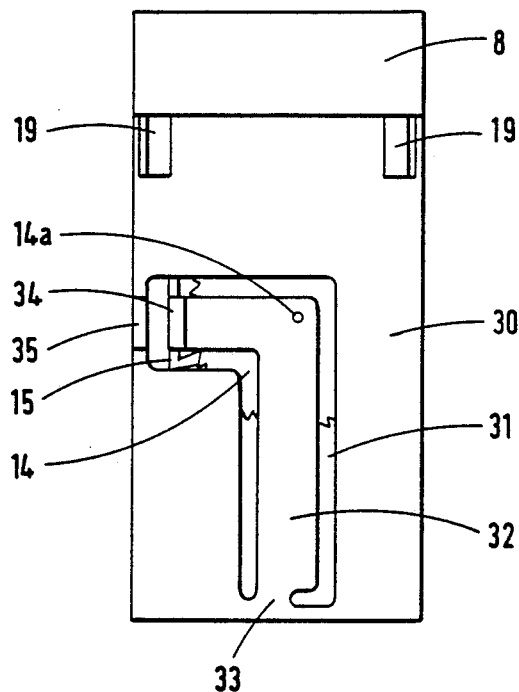

FIG. 2b shows a device according to the invention viewed from the opposite side to FIG. 2. The view shows a plate 30 which forms a cover for the mechanism visible in FIG. 2b. A slot 31 is formed in the plate 30 to define a tongue 32, having the shape of an inverted L, connected to the remainder of the cover only by a narrow bridge 33. An upstanding lug 34 is formed on the base of the L and a similar lug 35 is formed on the remainder of the cover on the opposite side of the slot to the lug 34. The material, e.g. plastics material, of which the plate is formed is sufficiently resilient that a user can urge the lugs towards one another, for example by gripping them between a thumb and finger, in which process flexing about the bridge 33 occurs. The axle 14a on which the wheel 14 rotates is mounted in the tongue 32, so that urging the lugs 34 and 35 together moves the wheel out of engagement with the rack 20. This enables the rack 20 to slide down to the end position in which it represents a value of zero doses having been dispensed. In this way the counter is reset to zero. Thus, when one container has been dispensed the counter can be removed, reset to zero, and mounted on a full container, and in this way can be reused many times.

FIGS. 3 and 4 show a medical inhalation device which comprises a tubular housing 101 in which an aerosol container 102 can be located. The housing 101 is open at one end which will hereinafter be considered the top of the device for convenience of description. The housing 101 is closed at the other end. An outlet 103 leads laterally from near the closed end of the housing 101. In the illustarted embodiment, the outlet 103 is in the form of a mouthpiece intended for insertion into the mouth of a patient, but it may, if desired, be designed as a nozzle for insertion into the nostril of a patient.

The aerosol container 102 has an outlet valve member 104 at one end. This valve member can be depressed to release a dose from the aerosol container or, alternatively, the valve member 104 can be fixed and the main body of the container can be moved relatively to the valve member 104 to release a dose. The aerosol container 102 is located in the housing 101 so that one end protrudes from the open top of the housing as shown clearly in FIG. 4. Spacer ribs, not shown, may be provided inside the housing to hold the external surface of the container spaced from the internal surface of the housing. A support or stem block 105 is provided at the lower end of the housing 101 and has a passage 106 in which the valve member 104 of the aerosol container 102 can be located and supported. A second passage 107 is provided in the support 105 and is directed towards the interior of the outlet 103. Thus, when the parts are in positions shown in FIGS. 3 and 4, the protruding portion of the aerosol container 102 can be depressed to move the container 102 relatively to the valve member 104 so that the valve will be opened and a dose of medicament contained in the aerosol will be discharged through the passage 107 into the outlet 103 from which it can be inhaled by the patient. One dose will be released from the aerosol container each time it is fully depressed.

An actuator and container retainer member in the form of a ring 108 is guided for sliding movement in the housing 101. Locating lugs 109 protrude from the ring 108 and slide in slots 110 in the wall of the housing. The aerosol container 102 is fitted in the ring 108 in such a way that once it is fitted therein it cannot be removed therefrom and also so that the ring will move with the container 102 when it is depressed to open the outlet valve of the aerosol container. The fact that the aerosol container cannot be removed once it has been fitted prevents misuse or abuse of the product by replacement with an alternative product which may be detrimental or even dangerous to the wellbeing of a patient and contrary to medical instructions.

A driving arm 111 extends from the ring 108 through a slot 112 in the wall of the housing 101 into an indicator compartment 113. The driving arm 111 engages a ratchet wheel 114 in the indicator compartment. The ratchet wheel co-operates with a ratchet pawl 115. When the aerosol container 102 is depressed, the driving arm 111 moves downwards and forwards to the centre of the ratchet wheel 114, so engaging the next adjacent ratchet tooth. When the aerosol container 102 is released, the driving arm 111 moves upwards causing the ratchet wheel 114 to rotate the distance of one tooth. Rotatable with the ratchet wheel 114 is a spur gear 115A which engages a toothed indicator wheel 116. Thus, the indicator wheel 116 rotates one step for each dose dispensed by depression of the body of the aerosol container 112. The front of the indicator housing 113 has a window 117 through which a portion of the indicator wheel 116 is indicated. This indicator wheel can be given suitable markings which are displayed through the window when the given markings registers with the window. Thus, in the embodiment illustrated the indicator wheel has markings "$\frac{1}{4}$", "$\frac{1}{2}$", "$\frac{3}{4}$", "F", and "E". The markings "F" and "E" respectively denoting full and empty. Any suitable markings may be made on the indicator wheel. For example, the wheel can be marked with different colours at different positions so that, for example, when a red portion is displayed through the window, the patient will know that a new inhalation device must be obtained. In other alternatives, the indicator wheel may be marked with numbers to indicate either the number of doses dispensed from the aerosol container or the number of doses remaining to be dispensed. In a convenient arrangement, the indicator wheel is arranged to display that the aerosol container is empty after 200 doses have been dispensed, in that case the container having been charged with, say, 220 doses, to allow a margin of error.

The device illustrated in FIGS. 5 and 6 is modified so that the ratchet wheel 114 will drive a single worm 118 which in turn drives an indicator rack 119 having a row of projections engageable by the worm. The other parts of the device designated by the same references are used with reference to FIGS. 3 and 4.

In the modified device illustrated in FIGS. 7 and 8, the ratchet wheel 114 again rotates a spur wheel 115A which engages and drives an indicator rack 120. Other parts of the device have the same reference numerals that are used in the description with reference to FIGS. 3 and 4.

The invention has hereinbefore been described in relation to medical inhalation devices but it is apparent that the invention may be applied to any container having a depressable dispensing valve, to determine the quantity of product used or that which is left in the container.

We claim:

1. An aerosol dispenser comprising:
   (a) a housing in which an aerosol container can be located, an outlet leading from the housing and a support in the housing arranged to receive an outlet member of the aerosol container and having a passage through which the contents of the aerosol container may pass to the outlet, the outlet member being held stationary in the housing support and the body of the container moveable relative to the outlet and housing to dispense its contents in measured doses; and (b) a dose indicating device for indicating and number of doses dispensed from, or remaining in, the container, the said device comprising
  (i) a linearly movable indicator means mounted externally of the said housing and moveable relative to said housing and said container;
  (ii) a movement detecting member movable by movement of the body of the contaienr relative to the outlet member and housing and
  (iii) means mechanically interconnecting the movement detecting member and the indicator means and responsive to movement of the movement detecting member relative to the housing to initiate movement of the indicating means incrementally.

2. A device according to claim 1 wherein the indicating means carries no numbers, letters, or like characters.

3. An aerosol dispensing device according to claim 1, wherein the dose indicating device comprises an indicator compartment disposed on a wall of the container-receiving housing, the movement detecting member comprising an actuator member mounted on, and carried by, the body of the aerosol container so as to be displaceable with respect to the outlet member, and hence with respect to the container-receiving housing, the said actuator member carrying an arm which extends into the said indicator compartment to operate the said mechanical means.

4. An aerosol dispensing device according to claim 3, wherein the said actuator member is arranged to be so mounted on the body of the aerosol container that it cannot be removed therefrom.

5. A device according to claim 1, wherein the movement detecting member comprises a ratchet wheel movable with one of the aerosol container and outlet member, and a ratchet wheel driving member is provided which is movable with the other of the aerosol container and outlet member and arranged to rotate the ratchet wheel through a predetermined step upon relative movement of the aerosol container and outlet member.

6. A device according to claim 5, wherein the indicator means comprises a toothed rack, and said mechanical means comprises a spur gear on said ratchet wheel which meshes with the toothed rack and drives it.

7. A device according to claim 5, wherein the indicator means comprises an indicator rack having a row of projections, and said mechanical means comprises a worm on said ratchet wheel which engages the row of projections and drives the rack.

8. A device according to claim 1, comprising an actuator member adapted to be removably mounted on the body of the aerosol container so as to be displaceable with respect to the outlet member, the actuator member comprising a further member which, during at least a portion of the movement of the actuator member, is held stationary with respect to the outlet member 9. A device according to claim 8, wherein the said further member is arranged to be held stationary with respect to the outlet member by abutment with said housing in which the aerosol container is received and in which the outlet member is supported during relative movement of the container body.

10. A device according to claim 8, wherein the actuator member comprises a ring-shaped cap adapted to be mounted on an end of the body of the aerosol container.

11. A device according to claim 8 comprising means for resetting the indicator means to zero.

* * * * *